United States Patent [19]

Hirsch et al.

[11] 4,320,111

[45] Mar. 16, 1982

[54] IMMUNOLOGIC COMPOSITIONS METHODS OF PREPARATION AND USE

[75] Inventors: Michael A. Hirsch, East Windsor, N.J.; Douglas S. Irvine, Rosemere; John Krupey, Montreal, both of Canada

[73] Assignee: American Home Products Corporation, New York, N.Y.

[21] Appl. No.: 127,630

[22] Filed: Mar. 6, 1980

Related U.S. Application Data

[63] Continuation-in-part of Ser. No. 806,563, Jun. 14, 1977, abandoned.

[51] Int. Cl.$^3$ .................... G01N 31/06; G01N 33/48; G01N 33/54; G01N 33/74
[52] U.S. Cl. .................... 424/12; 23/230 B; 260/112 R; 260/112 B; 424/3; 424/8; 424/11; 424/13; 424/101; 424/105; 424/111; 424/177; 435/4; 435/7
[58] Field of Search .................... 424/3, 8, 11, 12, 13, 424/101, 105, 111, 177; 23/230 B; 260/112 R, 112 B; 435/4, 7

[56] References Cited

U.S. PATENT DOCUMENTS

| | | | |
|---|---|---|---|
| 3,236,732 | 2/1966 | Arquilla | 424/12 |
| 3,269,905 | 8/1966 | Damaskus et al. | 206/459 |
| 3,322,634 | 5/1967 | Fulthorpe | 424/12 |
| 3,639,558 | 1/1972 | Csizmas | 424/12 |
| 3,689,633 | 9/1972 | Sanae | 424/12 |
| 3,714,345 | 1/1973 | Hirata | 424/12 |
| 3,715,427 | 12/1973 | Hirata | 424/3 |
| 3,862,302 | 1/1975 | Price et al. | 424/12 |
| 3,879,510 | 4/1975 | Kitajima | 424/12 X |
| 3,914,400 | 10/1975 | Shulman | 424/12 |
| 3,925,541 | 12/1975 | Hirata | 424/12 |
| 3,987,159 | 11/1976 | Spona | 424/12 |
| 3,991,174 | 11/1976 | Grundman | 424/12 |
| 3,991,175 | 11/1976 | Grundman | 424/12 |
| 3,992,514 | 11/1976 | Donini | 424/12 |
| 4,048,325 | 9/1977 | Packer | 424/3 |
| 4,069,352 | 1/1978 | Parsons | 422/61 |
| 4,123,509 | 10/1978 | Banik | 424/12 |
| 4,138,214 | 2/1979 | Givner | 424/12 |

FOREIGN PATENT DOCUMENTS

| | | | |
|---|---|---|---|
| 2187909 | 2/1974 | France | 424/12 |
| 1036591 | 7/1966 | United Kingdom | 424/12 |

OTHER PUBLICATIONS

Moreau, Chem. Abs., vol. 81, 1974, Ab. No. 103151b.
Gyenes, Immunochem, vol. 1, 1964, pp. 43–48.
Wide, Acta Endocrinol., Supp. 70, 1962, pp. 11–111.
Wide, Acta Endocrinol., vol. 35, 1960, pp. 261–267.
Ling, Brit. J. Haemat, vol. 7, 1961, p. 299.
Bing, PSEBM, vol. 124, 1967, p. 1166.
Herbert, in Handbook Exptl. Immunol, 2nd Ed. (Weir, Ed.) Blackwell Sci. Pub. London, 1973, pp. 20.1–20.16.
Goldstein, AJCP, vol. 46, 1966, pp. 48–53.
Priest, Med. Cytogenetics & Cell Culture, Lea & Febiger, Phila., 2nd. Ed., 1977, p. 267.
Williams (Ed.) Methods in Immunol. & Immunochem., Acd. Press, NY, vol. 5, 1976, pp. 109, 110, 116, 117, 120–125.

*Primary Examiner*—Anna P. Fagelson
*Attorney, Agent, or Firm*—Adley F. Mandel

[57] ABSTRACT

This invention relates to immunologic compositions comprising pyruvic aldehyde stabilized erythrocytes sensitized with an antigen by coupling of the stabilized erythrocytes to the antigen with bifunctional molecules, and to methods for preparing these compositions. Also disclosed are antiserum compositions which may be utilized with the described stable, sensitized erythrocytes of this invention as reagents in hemagglutination tests, and methods for their preparation. The invention further comprises lyophilization of these compositions and siliconized vials for use with the reagents of this invention.

18 Claims, No Drawings

IMMUNOLOGIC COMPOSITIONS METHODS OF PREPARATION AND USE

This is a continuation-in-part of U.S. Ser. No. 806,563, filed June 14, 1977, now abandoned.

BACKGROUND OF THE INVENTION

The development of reliable immunologic compositions useful as reagents in immunoassays to determine the presence or absence of antigens or antibodies in a test fluid has and continues to be a sought after goal. One approach which has received a great deal of attention has been the development of reagents for hemagglutination and hemagglutination inhibition systems. These systems employ red blood cells also known as erythrocytes which, for use, are joined with antigenic or antibody substances so as to provide an indicator system which can be used to detect the homologous antibody or the antigenic substance itself.

An early development in hemagglutination inhibition or passive hemagglutination tests was described by Wide and Gemzell, Acta Endocr. 35(1960) 261. They established that the red blood cells (Rbc) coated by or attached to the antigen must be stabilized to be useful hemagglutination inhibition tests, otherwise the red blood cells would need to be fresh daily. While Wide et al. stabilized the erythrocytes before attachment of the antigen, others have stabilized following attachment of the antigen.

Stabilization of Rbc was originally described by Boyden using formaldehyde, J. Exp. Med., 93, 107 (1951) and the concept was extended by Wide, Acta Endocr., supp. 70, 41(1962), when following pretreatment of formaldehyde treated RBC with tannic acid, it was shown that hCG could be absorbed onto the cell surface of the Rbc.

Ling, Brit. J. Haemat., 7, 229(1961), also showed the pyruvic aldehyde could beneficially replace formalin and that pretreatment with tannic acid was not necessary for antigen attachment. However for stabilization, Ling decreed that 48 hours at $+4°$ was necessary. But, the coated erythrocytes are unstable and are also time consuming to prepare.

One approach to improving stability and also of obtaining erythrocytes with higher hemagglutination titers were disclosed in U.S. Pat. No. 3,714,345; 3,715,427 and 3,925,541. There the erythrocytes were treated sequentially with pyruvic aldehyde and then formaldehyde for periods in excess of 12 hours for treatment prior to coating the thus stabilized erythrocyte with an antigen or antibody. The double aldehyde treated erythrocytes were in some cases further subjected to a lengthy freeze-thaw cycle at very low temperatures.

Another approach to obtain antigen sensitized erythrocytes was through the use of bivalent reagents as coupling agents between antigens and erythrocytes, e.g., bis diazotized benzidines illustrated in U.S. Pat. No. 3,236,732; various diols and quinones described in U.S. Pat. No. 3,322,634; toluene-2,4-diisocynates described in Immunochemistry 1:43(1964); etc. Since even the coupling coated erythrocytes are still readily susceptible to decomposition, formaldehyde treatment was usually employed prior to coating with antigen or simultaneously as described in U.S. Pat. No. 3,987,159 where the coupling agent employed was glutaraldehyde. In still a different approach described in U.S. Pat. No. 3,991,175, glutaraldehyde was also utilized as a coupling agent but gelatin was used to stabilize the composition.

The various compositions and methods already noted and numerous others suffer individually from various disadvantages such as instability, lack of reproducibility, false positive results, low hemagglutination titres, cost or time of preparation, and others.

It has now been found that the compositions and methods of this invention demonstrated in part by use in hemagglutination tests, provide a superior grade of stabilized, sensitized cells. The composition of this invention have higher hemagglutination titres, are stable for long periods of time, and give reproducible patterns and results. Another advantage of the herein disclosed invention is the stability of results obtained. For example, in utilizing a commercially available reagent the hemagglutination patterns change with time. Thus, in a pregnancy test, a negative result, i.e., complete hemagglutination within 2 hours, will change over 24 hours to show a quasiinhibition pattern; results recorded from 2-24 hours at room temperature will therefore indicate a significant number of false positive results. However, utilizing the composition and methods of this invention, results are obtained within 2 hours of testing and will not change for about 11 days thereafter or more. Other advantages will become apparent as the description of the invention unfolds.

SUMMARY OF THE INVENTION

The present invention comprises an immunologic composition of pyruvic aldehyde stabilized erythrocytes sensitized with a polypeptide or glycoprotein antigen, said stabilized erythrocytes being coupled to said antigen with a bifunctional molecule selected from glutaraldehyde, glyoxal, succinaldehyde, hexamethylene diisocyanate, toluene 2,4-diisocyanate, dimethyl suberimidate, and the method of producing same.

Another aspect of this invention comprises an antiserum composition and a method for its production. A further aspect of this invention comprises the disclosed compositions in lyophilized forms and their preparation and use in hemagglutination tests. Yet another aspect of this invention comprises a siliconized vial containing the reagent within which the hemagglutination test is performed.

DETAILED DESCRIPTION OF THE INVENTION

The present invention relates to an immunologic composition comprising pyruvic aldehyde stablized erythrocytes sensitized with a polypeptide or glycoprotein antigen selected from chorionic gonadotrophin, pregnant mare's serum gonadorophin, carcino embryonic antigen, luteinizing hormone, follicle stimulating hormone, human menopausal gonadotrophin, and thyroid stimulating hormone, said stabilized erythrocytes being coupled to said antigen with a bifunctional molecule selected from glutaraldehyde, glyoxal, succinaldehyde, hexamethylene, diisocyanate, toluene-2,4-diisocyanate, and dimethyl suberimidate. However, it is preferred to use as the bifunctional molecule for coupling glutaraldehyde, hexamethylene diisocyanate and dimethyl suberimidate.

The invention further comprises the described immunologic composition wherein the erythrocytes are dimethyl suberimidate stabilized erythrocytes. In this composition the coupling agent or bifunctional molecule would include all the coupling agents previously described except for the same dimethyl suberimidate.

According to the present invention a composition of stabilized red blood cells (erythrocytes) sensitized with a polypeptide or glycoprotein such as, human chorionic gonadotrophin (hCG) is prepared as one component in a two component reagent system. Stabilization of the erythrocytes is first accomplished by taking freshly drawn whole blood, generally from sheep, and immediately mixing it with an equal volume of an isotonic sterile anticoagulant, such as, Alsever's solution. The erythrocytes are then separated by centrifugation and washed with physiological saline. Pyruvic aldehyde reagent is prepared in physiological saline. Phosphate buffer and a suspension of washed erythrocytes in saline are added to the pyruvic aldehyde reagent. The suspension is then preferrably incubated at 37° C. for three hours with occasional agitation. Subsequently the stabilized red blood cells are thoroughly washed with saline. The pyruvic aldehyde stabilized cells (PAC) may then be stored at 4° C. as a 10% suspension in saline containing 0.1% sodium azide as a preservative, for at least a year, if desired. To sensitize the stabilized cells with hCG, the pyruvic aldehyde treated cells are washed with dilute saline and then suspended in a phosphate buffer containing hCG. To this suspension is added glutaraldehyde in normal saline. The mixture is then incubated, for example, at room temperature for about 2 hours under constant agitation and the cells are removed by centrifugation and washed not less than 3 times with phosphate buffered saline. Optionally, the sensitized cells are suspended in phosphate buffered saline containing as little as 0.2% normal rabbit serum in which complement had previously been fixed by heating at 56° C. for about 30 minutes and from which non-specific agglutinins, interfering proteins, had previously been removed by serial adsorption with an equal volume of pyruvic aldehyde stabilized cells. Sensitized cells may then be stored at 4° C. Alternatively, in place of normal rabbit serum, one could use any properly treated stabilization agent including properly adsorbed, complement fixed serum proteins. Illustrative of such stabilization agents are gelatin, dextrans, polyvinyl pyrrolidone, albumins and water soluble carboxymethyl celluloses.

The hCG used for sensitization of the stabilized cells, illustrated above may be of various grades of purity. For example material which assays, biologically, at approximately 2,500 I.U./mg may be employed. Alternatively, more purified hCG preparations, for example, a preparation assaying at approximately 10,000 I.U./mg or 14,000–16,000 I.U./mg may be utilized in the sensitization of the aforementioned stabilized red blood cells. Again the β sub-unit of hCG may also be utilized as the antigen on the red blood cell. It is generally preferrable to use the more purified hCG in the stabilized, sensitized erythrocyte compositions of this invention.

While the invention has been illustrated primarily using mammalian erythrocytes, such as those from sheep, these stabilized, sensitized erythrocytes may also be prepared from avian or reptilian red blood cells, which being nucleated settle more rapidly than mammalian erythrocytes. In this way the results from haemagglutination tests may be obtained within 30 minutes or sooner. The speed of the haemagglutination reaction is proportional to the buoyant density of the nucleated cell; thus as the buoyant density increases, less time is required to obtain results. Furthermore, whereas the invention was illustrated using Alsever's solution as the isotonic sterile anticoagulant, the freshly drawn whole blood may be optionally mixed with heparin sodium, EDTA, or sodium oxalate.

The described stabilized, sensitized erythrocyte composition together with their antiserum compositions are most useful in hemagglutination and hemagglutination inhibition (passive hemagglutination) methods for determining the presence or absence of a particular antigen or antibody in the test fluid being examined, usually a body fluid such as urine or serum. Thus determining the presence or absence of a pregnant condition in a female animal can be based on a hemagglutination method for determining the presence of chorionic gonadothrophin which comprises mixing the erythrocyte composition of this invention with a chorionic gonadotrophin antiserum and with the urine of test subject and, following a suitable incubation period, visually observing the results, whereby if said gonadotrophin is not present agglutination of the erythrocytes occurs upon standing whereas if said gonadotrophin is preset, no such agglutination occurs. A method for determining the presence of luteinizing hormone in a woman and thereby the day of ovulation may also be done utilizing the compositions of this invention wherein the antigen is human chorionic gonadotrophin as described in U.S. Pat. No. 4,123,510 issued Oct. 31, 1978, of Givner and Banik filed of even date herewith, hereby incorporated by reference. Similarly, pregnancy in a mare may be determined utilizing as the antigen pregnant mare's serum gonadotrophin and a composition utilizing carcino embryonic antigen would be useful in a blood test for cancer. Other uses for the compositions of this invention are described therein.

As illustrated below utilizing as the antigen, hCG it is hypothesized that the superior properties of the compositions of this invention are due to the coupling of the stabilized erythroycytes to the hCG by means of a chemical reaction between the amino functions of the erythrocytes and the hCG and the difunctional glutaraldehyde. The suggested course of reaction of glutaraldehyde is as follows:

(a) Aldol condensations:

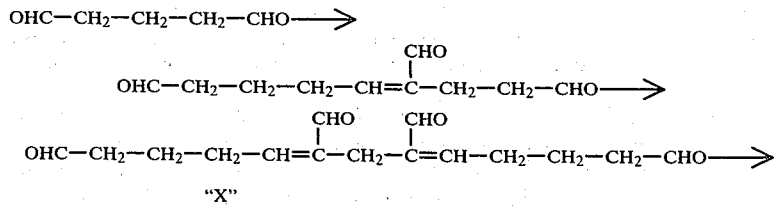

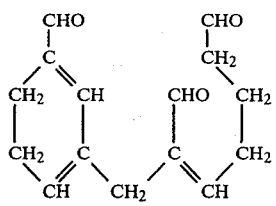

-continued (b) Cross-linking reactions:

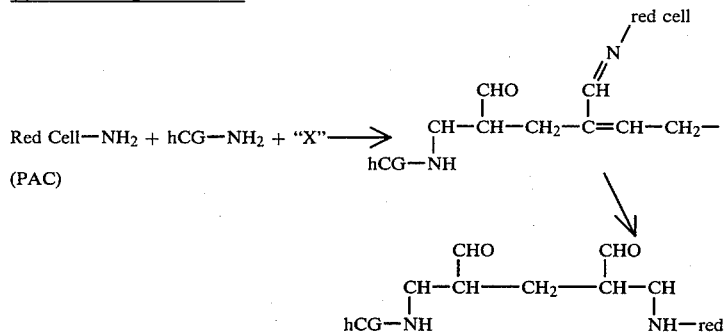

The reaction with hexamethylene diisocyante proceeds in the following fashion:

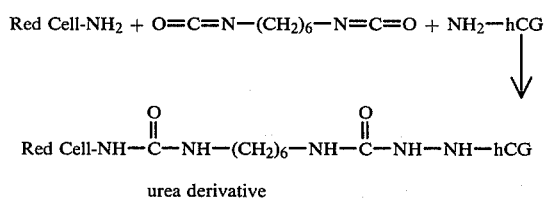

urea derivative

In order to conduct the passive haemagglutination tests contemplated by this invention it is necessary to prepare an antiserum composition to be used in conjunction with the antigen sensitized erythrocytes previously described. Depending on the test hCG which assays biologically as low as 2500 I.U./mg may be employed. Alternatively more purified hCG preparations that assay at approximately 10,000 I.U./mg, 15,000 I.U./mg or higher may be employed. It is preferred to utilize highly purified hCG and most preferred to use the β-subunit of hCG in preparing the antiserum of this invention to obtain greater specificity. An example of highly purified β-hCG and a method of producing same is reported in U.S. Pat. No. 4,123,343 issued Oct. 31, 1978, of Krupey and Welchner, filed of even date herewith, herein incorporated by reference.

The antiserum compositions are generally prepared by immunizing a host animal with the desired antigen thereby producing antibodies to that antigen which may be obtained in the serum separated from the host animal. A difficulty in the past has been that the hCG antigen has had other antigen impurities present, thus undesirable antibodies were also produced. A hemagglutination method utilizing such an antiserum composition would thus process undesirable cross reactivity.

The antisera composition of this invention is diluted either in microtitre slides or in a tube titration to determine the maximum dilution of antisera which can still agglutinate the red blood cell. The dilution is then adjusted when utilized in a method for determining pregnancy so that the anti-hCG serum has a sensitivity to hCG of about 100–150 m I.U./test. The acceptable antisera will also have a cross reactivity of less than 25% particularly against other glycoprotein hormone antigens. Thus an antisera sensitive to 100 m I.U./test of hCG would at the same time have a sensitivity to 400 m I.U./test or more of hLH or hMG. This highly specific antiserum composition obtained using highly purified β-hCG as the antigen, will detect early pregnancy via the presence of small amounts of hCG and also minimizes the possibility of obtaining false positives in the passive haemagglutination inhibition test. A method and apparatus for use of the herein described reagents is described in U.S. Pat. No. 4,123,509, issued Oct. 31, 1978 of Givner et al and filed Apr. 11, 1977, herein incorporated by reference.

While the compositions of this invention may be utilized in aqueous composition, it is preferred to lyophilize these compositions for use in the particular hemagglutination method under consideration. The compositions may be lyophilized into two separate pellets by methods known to those skilled in the art such as that described in U.S. Pat. No. 3,862,302. That disclosure, however, does not teach how to make lyophilized compositions containing in either the antiserum or the stabilized erythrocytes enough buffer for complexing the interfering calcium ions present in urine. Rather it involves the use of a third lyophilized pellet containing the necessary buffers or as in a commercially available pregnancy test a separate buffer composition which is reconstituted at the time of its use.

The compositions of this invention may also be lyophilized into a single layered cake, as described in U.S. Pat. No. 3,269,905. Also while a suitable chelating agent may be included within the lyophilized compositions of this invention to remove quantities of calcium present in a urine test sample, the compositions of this invention without added chelating agent may be utilized with urine and/or ultraconcentrated urine which has been passed thru a filter in which is placed a styrene divinyl benzene copolymer containing imide acetate functional groups (CHELEX 100 or DOWEX CHELATING RESIN A-1).

The physical characteristics of the vial in which the immunologic reagents e.g., the Rbc preparation described in this invention together with a suitable antiserum and appropriate buffers which are to be used in passive haemagglutination tests, must be properly defined. Pyrex culture tubes have been subjected to various physical pretreatments prior to utilization of the immunologic reagents, described herein in passive haemagglutination tests. We have found that round bottomed siliconized glass tubes having an I.D. of 12-16 mm is preferrable in order to obtain reproducible flocculation times and reproducible agglutination patterns.

The invention is further illustrated in the following examples:

EXAMPLE 1

Whole sheep blood was collected directly into Alsevers solution so that the final ratio of sheep blood to Alsevers solution was 1:1. For the purpose of this invention it has been established that the Rbc concentration or packed cell volume (pcv) of such a mixture must be in the range of 20-25% (i.e., a hematocrit of 40-50%) and preferably, 22%. The cells from 100 ml of such a mixture were collected by centrifugation and washed three times with normal, saline solution, i.e. 0.9% (w/v) sodium chloride in distilled water. The preferred volume of saline per wash is 320 ml but may be in the range of 100-500 ml. After washing, the cells will suspended in normal saline solution at a concentration of 20%. A mixture of pyruvic aldehyde (64 ml of 25% aqueous solution) and normal saline (120 ml) was adjusted to pH 7.0 using a 10% w/v aqueous sodium carbonate solution. To this mixture of pyruvic aldehyde and saline was added the abovementioned cell suspension (100 ml at 20%), followed by phosphate buffer (28 ml., 0.15 M, pH 8.0). This stabilization mixture was then incubated at 37° C. for 3 hours, the mixture being shaken vigorously once every 30 minutes.

The cells were then collected by centrifugation and washed 4 times with normal saline solution utilizing preferably 320 ml of saline per wash. The stabilized cells may then be stored as a suspension, preferably 10%, in normal saline containing, for example, 0.1% sodium azide as a preservative. This is stable at least a year at +4° C.

EXAMPLE 2

Stabilized cells as described in Example 1 (10 ml of about a 10% suspension) were collected by centrifugation and washed 3 times with normal saline solution, preferably 40 ml for each wash. Alternatively, one may of course use unstored cells directly from example 1. These washed cells were then suspended in a solution of hCG (100 μg in 100 μl of 0.5 M phosphate buffer) contained in 0.15 M phosphate buffer (8.65 ml, pH 7.4). To this suspension was added a glutaraldehyde reagent (1.75 ml), prepared by diluting a 25% aqueous solution of glutaraldehyde (1 ml) in normal saline (9ml).

The sensitization mixture was thoroughly agitated and then gently mixed for 2 hours at room temperature. The cells were collected by centrifugation and washed, preferably 4-5 times, with 0.15 M phosphate buffered saline (pH 7.4).

The sensitized cells are then suspended in 0.15 M phosphate buffered saline (39 ml, pH 7.4) containing 0.2% of normal rabbit serum in which complement had previously been fixed by incubating at 56° C. for 30 minutes and from which non-specific agglutinins had been adsorbed by triple treatment with stabilized cells (Example 1). The removal of non-specific agglutinins is illustrated in Example 3.

EXAMPLE 3

Prior to use for the removal of non-specific agglutinins from normal rabbit serum, stabilized cells as prepared in EXAMPLE 1, were washed with normal saline (5 volumes saline: 1 volume of 10% cell suspension) and re-suspended in saline solution at 10%. Equal volumes of rabbit serum and a 10% suspension of stabilized red blood cells were then incubated at room temperature for 30 minutes. The cells were collected by centrifugation, discarded and the process repeated 2 more times, using collected cells as opposed to a 10% suspension.

Alternatively, the last adsorption may be allowed to proceed at +4° C. for 18 hours. Under the conditions described in this example, the normal rabbit serum has been diluted 1:1 with saline. It should be understood, however, that for this adsorption it is possible to utilize collected cells as opposed to a 10% suspension which would not result in a dilution of the normal rabbit serum.

EXAMPLE 4

Utilizing the methods of example 2, but with pregnant mare's serum gonadotrophin as the antigen, a stable sensitized composition was also prepared and satisfactorily evaluated.

EXAMPLE 5

Lyophilized cakes were prepared as follows. A suspension of the stabilized, sensitized red blood cells (S-PAGC) was washed about 3 times with a 0.15M phosphate buffer solution adjusted to a pH of 7.4. The washed S-PAGC were then resuspended as a 0.415% v/v suspension in lyophilization buffer, LB, (LB used was 10 g sucrose, 10 ml of 1% merthiolate, 10 ml of NRS triply adsorbed, and q.s to 1 liter with 0.15 M phosphate buffered saline containing about 0.2% EDTA to a pH of 7.0). 300 μl of the cell suspension were then pipetted into different siliconized vials already in a test tube rack, and the rack containing the vials was immersed in an acetone-dry ice bath at about −70° C. and frozen. Dilutions of antisera and NRS, (which had been pretitrated and adjusted to give a predetermined sensitivity) were made with LB such that the proper concentration of antisera in NRS is contained in a 200 μl aliquot, was then pipetted onto the frozen cell layers in the bath.

The frozen reagents may then be stored at about −100° C. until lyophilization or lyophilized immediately. Lyophilization of thse reagents was then done in a freeze drier for at least 18 hours at 75-200 microns. Hg, while gradually reaching ambient temperatures. The vacuum was not permitted to be less than 75 microns to avoid spontaneous haemagglutination. The lyophilized reagents when stored at 4° C. are stable for at least 9 months.

EXAMPLE 6

Lyophilized pellets were prepared as follows:

A suspension of S-PAGC was washed as in example 5 and then resuspended as a 2.5% suspension in LB concentrated by a factor of 5 in all its components. This latter suspension was constantly agitated while a proportioning pump repeatedly delivered about 50 μl of the S-PAGC suspension into a liquid N₂ bath at −196° C. and the pellets were harvested in a petri dish. The antisera pellets were prepared similarly but may optionally have incorporated within the LB 2.5% of polyvinyl pyrrolidone or dextran. The pellets may be stored as the cakes are stored in example 4 or transferred immediately to the freeze drier. Pellets have been dried satisfactorily at about, 50–200 microns Hg for about 18 hours, with the temperature finally reaching room temperature or in some cases 35° C. The pellets were stored in a dessicator at room temperature until packing into siliconized vials. These pellets have been found to maintain their sensitivity and physical characteristics in long term stability studies at both 30° C. and 4° C.

EXAMPLE 7

Pretreatment with silicone is most beneficial as exemplified in Example No. 8. The method used for pretreatment with silicone is described under (e), whilst other pretreatments, used for comparative purposes, are described in (a) to (d).
(a) Untreated tubes used directly from the manufacturer.
(b) Pyrolyzed tubes prepared by heating at 560° C. (not more than 565° C.) for not less than 5 minutes.
(c) BSA coated tubes
  (i) Wash in 1% (w/v) bovine serum albumin with agitation, 20 sec.
  (ii) rinse in running distilled water, 3 times.
  (iii) dry overnight at 60° C.
(d) BSA-coated acid washed tubes
  (i) chromic-sulfuric acid wash, overnight soak.
  (ii) rinse in running tap water, 3 times.
  (iii) soak in 95% ethanol—one hours, 2 changes.
  (iv) rinse in running tap water, 2 times.
  (v) rinse in running distilled water, 3 times.
  (vi) dry overnight at 100° C.
  (vii) wash in 1% BSA with agitation, 20 sec.
  (viii) rinse in running distilled water, 3 times.
  (ix) dry overnight at 60° C.
(e) Siliconized tubes
  (i) Wash in 1% (v/v) SILICLAD (Clay Adams), a silane in aqueous alcohol solution, with agitation, 20 sec.
  (ii) rinse in running distilled water, 6 times.
  (iii) dry overnight at 100° C.

EXAMPLE 8

The following results were observed with the pretreated tubes of example 7.
  (i) Untreated, pyrolized, BSA-treated and acid washed BSA-treated vials lead to collapsed cell matts, or matts of rough appearance, when a haemagglutination pattern should result using the reagents of this invention.
  (ii) With the vials pretreated as in (i) above, the transition from haemagglutination to inhibition of haemagglutination is irregular.
  (iii) Vials pretreated with silicone demonstrate smooth haemagglutination patterns.
  (iv) In vials pretreated with silicone, the transition from haemagglutination to inhibition of haemagglutination, in the presence of increasing amount of antigen, is regular and the degree to which haemagglutination is inhibited is proportional to the increasing amount of antigen present.

A method for preparing the antiserum composition of this invention is illustrated in the following example.

EXAMPLE 9

| Antigen: β-hCG subunit | |
|---|---|
| Initial Challenge Solution (ICS) | |
| Tubercle bacillus | 5.0 mg |
| β-hCG | 200 μg |
| saline | 2 ml |
| complete Freund's adjuvant | 2 ml |
| Subsequent Challenge Solution (SCS) | |
| μ-hCG | 1.0 mg |
| saline | 5 ml |
| complete Freund's adjuvant | 5 ml |
| Booster Solution (BS) | |
| β-hCG | 100 μg |
| saline | 1 ml |

Each of the ICS and SCS are homogenized well until the suspensions are thick and creamy.

Immunization Protocol

Day 1—Three month old virgin female New Zealand white rabbits are injected with 2.0 ml of "ICS" at 30–50 intradermal sites.
Five hundred μl of crude *Bordetella pertussis* vaccine is injected at a separate intradermal site.
Day 14—Each rabbit is bled from the marginal ear vein.
Day 15—Each rabbit is injected with a total of 1.0 ml "SCS" in the hind foot pads.
Days 22, 29, 36, 43—Each rabbit is injected with a total of 1.0 ml "SCS" in multiple intradermal sites.
Day 49—Each rabbit is injected with 1.0 ml "BS" intravenously in the marginal ear vein.
Day 56—Each rabbit is bled from the marginal ear vein.
Thereafter, one ml of "BS" is injected intravenously every 6 weeks and the rabbits bled 5-7 days after each booster. The total time necessary to produce an antiserum using this combined multiple intendermal site-foot pad method of immunization will vary and is considered complete when the antibody titre which is constantly being monitored reaches a plateau.

The anti-serum is separated from the rabbit blood and complement may be fixed and the suspension adsorbed as described with the S-PAGC composition in example 2 and 3, a single adsorption usually being sufficient. Undiluted antisera or diluted antisera may be stored preferably at −100° C. in small aliquots.

We claim:
1. An immunologic composition comprising pyruvic aldehyde stabilized erythrocytes sensitized with a polypeptide or glycoprotein antigen selected from the group consisting of chorionic gonadotrophin, pregnant mare's serum gonadotrophin, carcino embryonic antigen, luteinizing hormone, follicle stimulating hormone, human menopausal gonadotrophin and thyroid stimulating hormone, said stabilized erythrocytes being coupled to said antigen with a bifunctional molecule selected from the group consisting of glutaraldehyde, glyoxal, succinaldehyde, hexamethylene diisocyanate, toluene 2,4-diisocyanate, dimethyl suberimidate.
2. The composition of claim 1, wherein said erythrocytes are selected from the group consisting of mammalian, avian, and reptilian erythrocytes.
3. The composition of claim 1, wherein said antigen is chorionic gonadotrophin and said bifunctional molecule is glutaraldehyde.

4. The composition of claim 1, wherein said antigen is chorionic gonadotrophin and said bifunctional molecule is hexamethylene diisocyanate.

5. The composition of claim 1, wherein said antigen is chorionic gonadotrophin and said bifunctional molecule is dimethyl suberimidate.

6. The composition of claim 1 which is lyophilized.

7. The composition of claim 3 which is lyophilized and wherein said chorionic gonadotrophin is human chorionic gonadotrophin.

8. The composition of claim 4 which is lyophilized and wherein said chorionic gonadotrophin is human chorionic gonadotrophin.

9. The composition of claim 5 which is lyophilized and wherein said chorionic gonadotrophin is human chorionic gonadotropin.

10. The composition of claim 1 which is lyophilized and wherein said antigen is pregnant mare's serum gonadotrophin and said bifunctional molecule is glutaraldehyde.

11. A method for preparing immunologic compositions of animal erythrocytes sensitized with antigens useful in passive haemagglutination tests which comprises:
   (a) collecting animal blood directly into Alsevers solution so that a final ratio of blood to Alsevers solution is 1:1 in this mixture and wherein the erythrocyte concentration packed cell volume of said blood is from about 20% to about 25%;
   (b) separating the erythrocytes from said mixture by centrifugation;
   (c) washing said erythrocytes with normal saline and then suspending said erythrocytes in normal saline at a concentration of about 20%;
   (d) mixing the suspension of erythrocytes with a buffered mixture of pyruvic aldehyde and normal saline, wherein said pyruvic aldehyde-erythrocyte mixture is phosphate buffered to pH 8.0;
   (e) incubating the stabilization mixture of step (d) at 37° C. for 3 hours, and collecting the stabilized erythrocytes by centrifugation followed by washing with normal saline;
   (f) suspending the stabilized erythrocytes in a phosphate buffered solution of antigen;
   (g) forming a sensitization mixture by thoroughly agitation the suspension of stabilized erythrocytes-antigen with a solution of a bifunctional molecule selected from the group consisting of glutaraldehyde, glyoxal, succinaldehyde, hexamethylene diisocyanate, toluene 2,4-diisocyanate and dimethyl suberimidate in saline;
   (h) mixing the sensitization mixture for a further 2 hours at room temperature;
   (i) collecting the sensitized erythrocytes by centrifugation and subsequently washing them with phosphate buffered saline;
   (j) suspending the sensitized erythrocytes in phosphate buffered saline containing normal rabbit serum wherein the complement of said rabbit serum had previously been fixed.

12. The method of claim 11 wherein said antigen is human chorionic gonadotropin and said bifunctional molecule is selected from glutaraldehyde, hexamethylene diisocyanate and dimethyl suberimidate.

13. The stabilized sensitized erythrocyte composition obtained by the method of claim 11 wherein said antigen is human chorionic gonadotropin and said erythrocytes are selected from the group consisting of mammalian, avian and reptillian erythrocytes.

14. The composition of claim 13 in lyophilized form.

15. A method for determining the presence of human chorionic gonadotropin in a human which comprises mixing the composition of claim 13 with a highly purified hCG antiserum and with ultraconcentrated urine of said human whereby if hCG is not present agglutination of the erythrocytes occurs upon standing whereas if hCG is present no such agglutination occurs.

16. The method of claim 15 wherein said antiserum is a $\beta$-hCG specific antiserum.

17. The method of claim 15 wherein said antiserum is adjusted to have a sensitivity to hCG of 100–150 mI.U. per test and a cross reactivity to other glycoprotein hormone antigens of less than 25 percent.

18. An immunologic composition comprising dimethyl suberimidate stabilized erythrocytes sensitized with a polypeptide or glycoprotein antigen selected from the group consisting of chorionic gonadotrophin, pregnant mare's serum gonadotrophin, carcino embryonic antigen, luteinizing hormone, follicle stimulating hormone, human menopausal gonadotrophin and thyroid stimulating hormone, said stabilized erythrocytes being coupled to said antigen with a bifunctional molecule selected from the group consisting of glutaraldehyde, glyoxal, succinaldehyde, hexamethylene diisocyanate and toluene 2,4-diisocyanate.

* * * * *